United States Patent [19]

Wuerschum

[11] Patent Number: 5,255,574
[45] Date of Patent: Oct. 26, 1993

[54] DEVICE FOR REMOVING AND INSERTING STOPPERS OF CONTAINERS FILLED WITH A LIQUID

[75] Inventor: Hans-Peter Wuerschum, Ostfildern, Fed. Rep. of Germany

[73] Assignee: Eastman Kodak Company, Rochester, N.Y.

[21] Appl. No.: 823,223

[22] Filed: Jan. 21, 1992

[30] Foreign Application Priority Data

Jan. 29, 1991 [DE] Fed. Rep. of Germany ....... 4102479

[51] Int. Cl.⁵ .............................................. B67B 7/02
[52] U.S. Cl. ........................................ 81/3.2; 81/3.32; 81/3.33; 81/3.42
[58] Field of Search ............. 81/3.2, 3.29, 3.25, 81/3.32, 57.18, 3.07, 3.31–3.39, 3.4, 3.42, 57.21

[56] References Cited

U.S. PATENT DOCUMENTS

| | | | |
|---|---|---|---|
| 1,598,392 | 8/1926 | Risser | 81/3.2 |
| 2,644,354 | 7/1953 | Schlageter | 81/3.42 |
| 3,589,742 | 6/1971 | Flick | 81/57.18 X |
| 4,217,798 | 8/1980 | McCarthy et al. | |
| 4,852,431 | 8/1989 | Frangel | 81/3.2 |
| 4,876,926 | 10/1989 | Muszak | |
| 4,982,553 | 1/1991 | Itoh | |
| 5,003,844 | 4/1991 | Barrow | 81/3.2 |

FOREIGN PATENT DOCUMENTS

| | | |
|---|---|---|
| 3141780 | 5/1983 | Fed. Rep. of Germany. |
| 2370680 | 11/1976 | France. |
| 1006759 | 6/1987 | Japan. |
| 62-006171 | 7/1987 | Japan. |
| 726526 | 3/1955 | United Kingdom. |
| 1245081 | 9/1971 | United Kingdom. |

OTHER PUBLICATIONS

*Patent Abstracts of Japan*, vol. 11, No. 177 (P-583) (2624) Jun. 6, 1987 & JP-A-62 006 171 (TOA Medical Electronics) Jan. 13, 1987.

*Primary Examiner*—D. S. Meislin
*Attorney, Agent, or Firm*—Peter J. Bilinski

[57] ABSTRACT

An analyzer is disclosed having a device for removing and inserting a stopper from and into the opening of a container for liquids arranged in a tray, particularly test tubes filled with body fluids, a gripper which performs rotary movements frictionally interacting with stopper and a lifting means feeding the container to the gripper and fixing it.

The gripper features three radially arranged clamping elements with rollers on an inner carrier member, said clamping elements being radially movable by control elements associated therewith and mounted on an outer hollow-cylindrical housing portion. The control elements are coaxially arranged in the form of a ring and each consists of a cam section having a small radius and a cam section having a larger radius, said sections being interconnected via a ramp and having a threshold.

4 Claims, 4 Drawing Sheets

DEVICE FOR REMOVING AND INSERTING STOPPERS OF CONTAINERS FILLED WITH A LIQUID

FIELD OF THE INVENTION

The invention relates to a device provided in an analyzer, such as those used for the testing of liquid analytes, to remove and insert a stopper from and into the opening of a container for liquids arranged in a tray, particularly test tubes filled with body fluids, a gripper which performs rotary movements frictionally interacting with the stopper and a lifting device feeding the container to the gripper and fixing it.

BACKGROUND OF THE INVENTION

Analyzers for the testing of liquid analytes are known having automatically and semi-automatically operating devices for removing and inserting stoppers of containers filled with liquids or samples.

From JP-AP 62 006 171 a device is known for removing and inserting a stopper from and into the opening of a container for body fluids arranged in a tray, wherein a tongue-shaped gripper performing lifting and rotating movements frictionally engages the stopper by means of two pivotable clamping jaws. The container is lifted from the tray by means of a clamping/lifting device and positioned and fixed beneath the gripper. Such a device is disadvantageous in that the pivoting movement of the jaws requires movement over a substantial distance, in a manner that can misalign the jaws. A better construction would be one in which the jaws are caused to translate or reciprocate only, as this movement is less likely to jar the containers.

From EP-AP 0 264 456 a device is known in which the stopper is withdrawn from the opening of the container. The device comprises two clamping jaws with needles and supports arranged on both sides of the container as well as an ejector for the stopper operating under spring force. Furthermore, a clamping/lifting device is provided for the container.

For removing the stopper, the container together with the stopper is urged in the direction of its longitudinal axis, that is to say vertically upwards against the ejector and then the clamping jaws are moved radially towards the stopper. In this way, the needles penetrate the stopper. Subsequently, the container is pulled downwards and withdrawn from the stopper by means of the clamping/lifting device. The stopper is removed by the ejector when the clamping jaws have returned to their home position.

Moreover, from the DE-OS 31 41 780 and US-PS 4,217,798 devices are known in which the stoppers are removed by means of a stripper which is arranged laterally with respect to the container and movable normal to its longitudinal axis, thereby pressing against the side of the stopper and then stripping the stopper off the container by tilting it.

It is desired to provide a device of the generic type by means of which stoppers made of different material and having different diameters can easily, reliably and jar-free be removed from and replaced into the opening of a container arranged in a tray. Moreover, the processing rate for the samples is to be increased considerably in order to meet the requirements of a quick and reliable diagnosis.

SUMMARY OF THE INVENTION

There is provided, in accordance with the invention, a device provided in an analyzer for removing and inserting a stopper from and into the opening of a container for liquids arranged in a tray, the device comprising means for gripping a stopper container, a gripper which performs rotary movements frictionally interacting with the stopper and means for feeding the container to the gripper and fixing it. The device is improved in that the gripper comprises plural radially arranged clamping elements, and control means for radially and translatably moving the clamping elements into and out of engagement with a stopper.

Preferably, the gripper features three radially arranged clamping elements which are radially movable by means of control elements associated therewith, in that the control elements are coaxially arranged in the form of a ring, and in that each control element is provided with a first cam section having a small radius to provide an inner radial contact position, and a second cam section having a larger radius to provide an outer radial contact position, said sections being interconnected via a ramp.

In this arrangement, the control elements are coplanar with the clamping elements at the time of engagement with the stopper.

The invention provides for each clamping element to contact the cam section via a roller under the action of a spring element and to be arranged on a carrier member of the gripper, the clamping elements forming with their inner end portions a circular opening which is smaller than the outer diameter of the stopper when the clamping element contacts the inner cam sections at the inner radial contact position, and larger than said outer diameter when the clamping elements contact the outer cam sections wherein the clamping elements and control elements are coplanar to one another.

The control elements are arranged at a hollow cylindrical housing portion of the gripper, said housing portion being arranged around the carrier member and the control elements being rotatable relative to the clamping elements or even jointly therewith about a pivot, i.e. the longitudinal axis of the gripper.

Additional features of an embodiment of the invention illustrated in the drawing as well as the subclaims will show the details of the device according to the invention.

DESCRIPTION OF THE PREFERRED EMBODIMENTS

Figure 1:
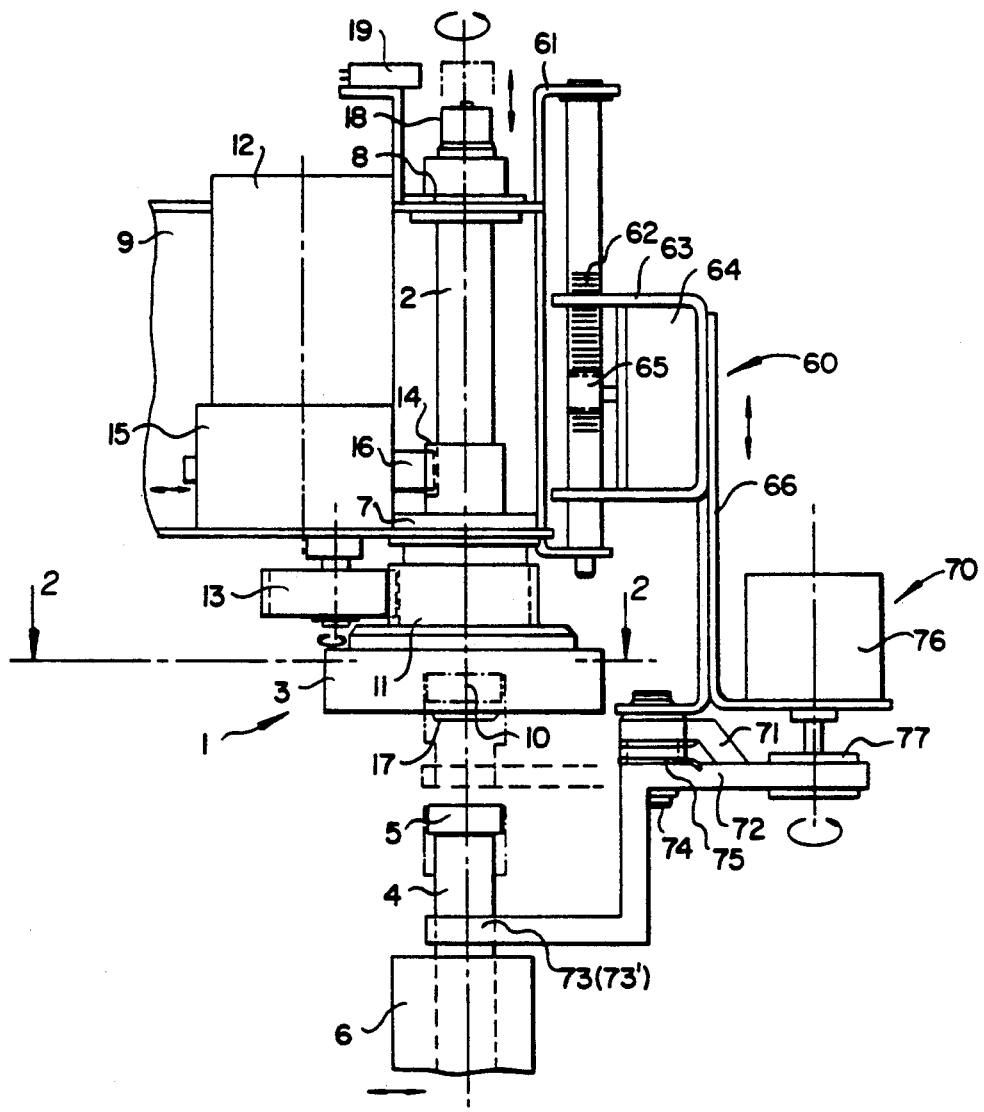
FIG. 1 shows a lateral view of the device according to the invention including a gripper, a lifting means and a tray holding a container.

A device illustrated in FIG. 1 consists of a gripper 1, a stepping motor 12, an electromagnet 15 and a lifting means 60 arranged on an outrigger 9.

The gripper 1 features a carrier member 2, a housing portion 3 and an ejector 17.

The longitudinal axis of the carrier member 2 designed in the form of a hollow cylinder is coaxial with pivot 10, the upper end portion of the carrier member being rotatably supported in a bearing 8 and, in the area of its lower end portion, in a bearing 7.

The housing portion 3 also having a hollow cylindrical shape is concentrically and rotatably mounted beneath the lower bearing 7.

The ejector 17 shaped as a cylinder rod is centrally arranged in carrier member 2 and movable along the axis of rotation located in pivot 10.

The electromagnet 15 is arranged laterally with respect to carrier member 2 and above bearing 7 and is provided with a locking pin 16 which is movable normal to the axis of rotation and in its initial position extends into a groove at the periphery of carrier member 2.

The stepping motor 12 is arranged beside carrier member 2 in the area of the electromagnet 15 and features a gear 13 on the vertically extending and downwardly oriented drive shaft which gear engages a toothed rim 11 mounted on the periphery of housing portion 3.

On the opposite side of carrier member 2, at the outer end portion of outrigger 9, a lifting means 60 is arranged which consists of a retaining clip 61, a vertically extending rack 62 retained by said clip, support bracket 63 forming upper and lower guides on rack 62, a drive motor 64, a supporting member 66 and a gripping device 70.

The drive motor 64 arranged on the support bracket 63 features a gear 65 on its horizontally extending drive shaft, said gear 65 engaging with rack 62.

The gripping device 70 retained on support bracket 63 by means of supporting member 66 consists of two horizontally oriented grip arms 71, 72, a leg spring 75 and a drive motor 76 with a radial cam 77 on its vertically extending and downwardly oriented drive shaft.

Both grip arms 71, 72 and the leg spring 75 are rotatably mounted on a vertically arranged pivot pin 74. A first side of the grip arms 71, 72 projects into the area of the radial cam 77 and a second side into the area of a tray 6 located in the processing position and equipped with containers 4. In this situation, tray 6 is positioned beneath gripper 1 and the longitudinal axis of container 4 is identical with the axis of rotation 10. The end portions of leg spring 75 contact the second side of the grip arms 71, 72 and urges it towards radial cam 77.

In the embodiment shown in the drawing the lifting means 60 is illustrated in an initial position, i.e. in a lowered position relative to rack 62.

In this position the grip arms 71, 72 of the gripping device 70 are arranged in an opened or outer position (not illustrated) in the area of container 4 and in an inner position at the radial cam 77.

In the processing position (dashed lines), i.e. end position, the lifting means 60 is located in an upper position and the grip arms 71, 72 are located in a closed inner position in the area of container 4.

Container 4 is embraced by the grip arms 71, 72 provided with jaws 73, 73' and shown in a position lifted from tray 6 so that the stopper 5 of container 4 extends into the gripper 1 and the ejector 17 is positioned in an upper end position. A stop means 18 arranged at the upper end portion of the ejector 17 is located within the actuating range of a switch 19 arranged in said upper end position.

Figure 2:
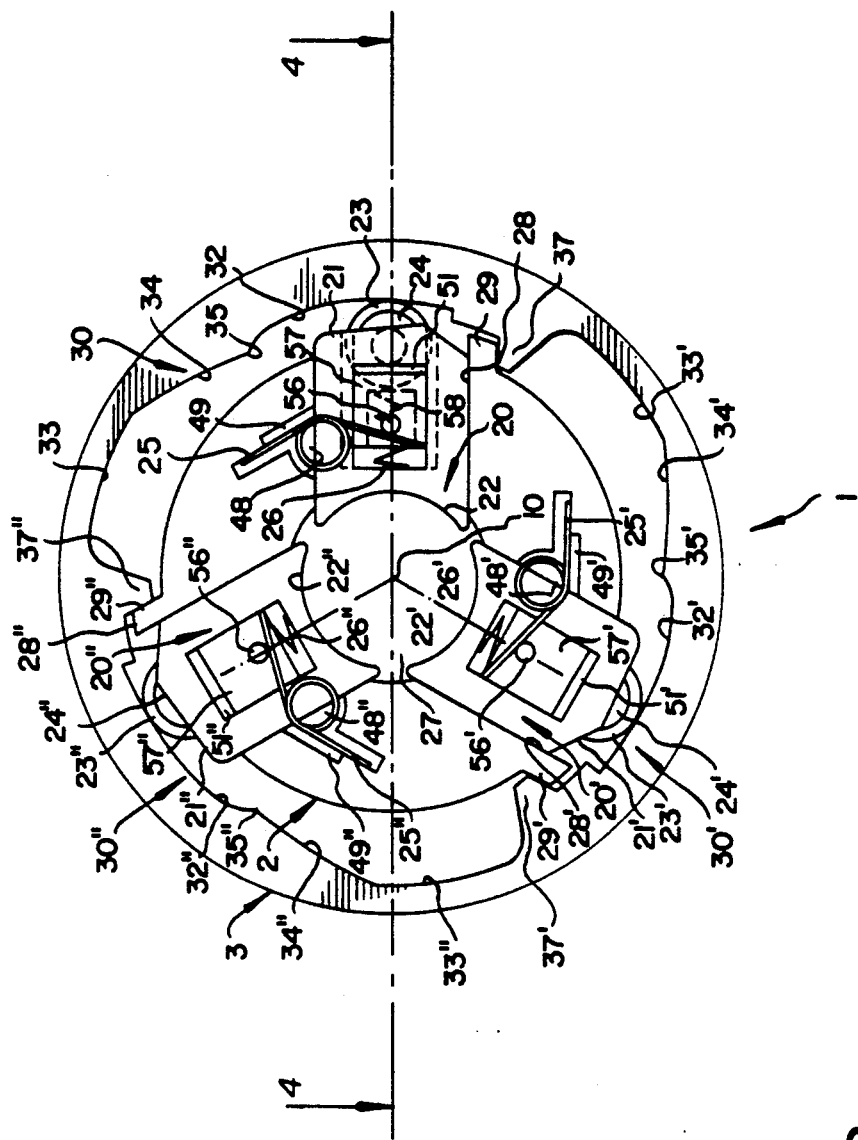
FIG. 2 shows a top view (cross-section along a line 2—2 in FIG. 1) of the gripper including the clamping, control and spring elements.

FIG. 2 shows the gripper 1 consisting of the carrier member 2 including three clamping elements 20, 20', 20" and the housing portion 3 including three control elements 30, 30', 30".

The carrier member 2 illustrated as an inner circular ring comprises three guide paths 28, 28', 28" for the clamping elements 20, 20', 20", said guide paths being evenly (120 degrees) distributed around pivot 10.

On one side of each guide path 28, 28', 28" at their outer end portions a stop means 29, 29', 29" is provided projecting beyond the periphery of carrier member 2.

The housing portion 3 illustrated as an outer circular ring shows on its inner side the control elements 30, 30', 30" which are associated with the clamping elements 20, 20', 20" and relative thereto or jointly therewith are arranged so as to rotate about pivot 10.

Each control element 30, 30', 30" features a first cam section 32, 32', 32" having a small radius forming an inner radial contact position. and a second cam section 33, 33', 33" having a larger radius and forming an outer radial contact position, which are connected via a ramp 34, 34', 34". Between the first, i e. the inner cam section 32, 32', 32" and the ramp 34, 34', 34" a threshold 35, 35', 35" is formed. Partitions 37, 37', 37" define the individual control elements 30, 30', 30". Control elements 30, 30' and 30" as shown in FIG. 2 are therefore coplanar with clamping elements 20, 20' and 20" within the ring defined by members 2 and 3.

At its outer end portion 21, 21', 21" each clamping element 20, 20', 20" features a radially movable roller support including a rotatably mounted roller 23, 23', 23" projecting beyond clamping element 20, 20', 20" and stop means 29, 29', 29" and contacting one of the cam sections of the control element.

The inner end portions 22, 22', 22" of the clamping elements 20, 20', 20" show a concave configuration and define a circular opening 27 which is smaller than the outer diameter of a stopper 5 when the clamping elements contact the inner cam sections 32, 32', 32" at the inner radial contact position and larger than said outer diameter when the clamping elements contact the outer cam sections 33, 33', 33"at the outer radial contact position.

On carrier member 2 beside the clamping elements 20, 20', 20" spring elements 25, 25', 25" are arranged on bearing pins 48, 48', 48" in the form of leg springs whose first legs are fixed to stop means 49, 49', 49" and whose second legs contact pins 56, 56', 56" of the roller supports 24, 24', 24". Each pin 56, 56', 56" is arranged on a guide member 57, 57', 57" of roller support 24, 24', 24" which member extends through a rectangular aperture 51, 51', 51" in clamping element 20, 20', 20". With respect to guide member 57, 57', 57", aperture 51, 51', 51" is longer in radial direction than the amount the threshold 35, 35', 35" projects from cam section 32, 32', 32".

Another spring element 26, 26', 26" shaped as a helical spring is located in a bore 58, 58', 58" of roller support 24, 24', 24" in the area of the inner end portion 22, 22', 22" of clamping element 20, 20', 20".

Both spring elements 25, 25', 25" and 26, 26', 26" show a radially outwardly directed action of force so that each of the clamping elements 20, 20', 20", i.e. the rollers 23, 23', 23", contacts a cam section, either at the inner or outer radial contact position.

Figure 3:
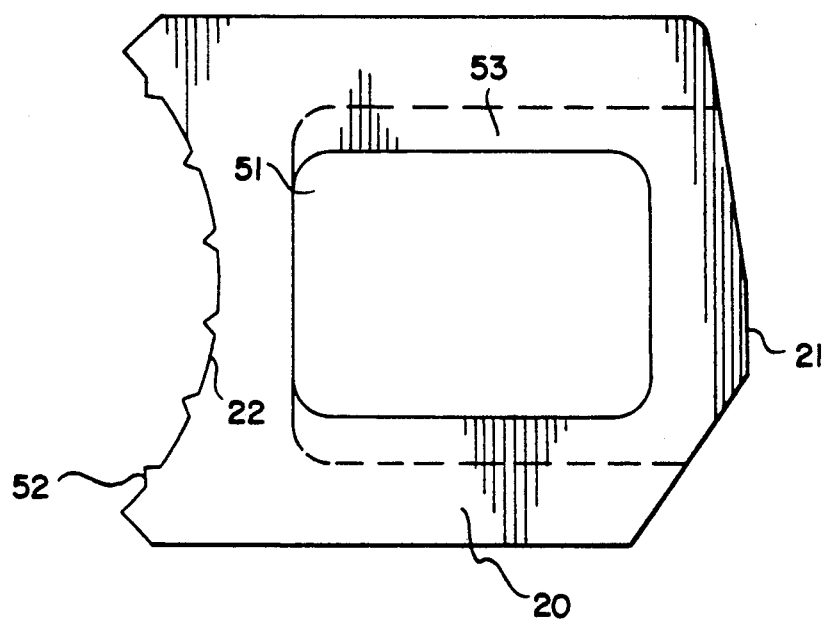
FIG. 3 is an enlarged top view of a clamping element according to FIG. 2.

The clamping element 20 shown in FIG. 3 comprises the aperture 51 described with respect to FIG. 2, a take up means 53 for the roller support 24 and pointed protuberances 52 at its inner end portion 22.

The pointed protuberances 52 are shaped as small spikes or corrugations, their dimensions and spaces between each other being selected such that an optimal grip for all admissible stoppers 5 is achieved.

Also, the height of the clamping elements 20, 20', 20" has been adapted to the height of the stoppers 5 so as to a achieve an optimal grip.

Figure 4:
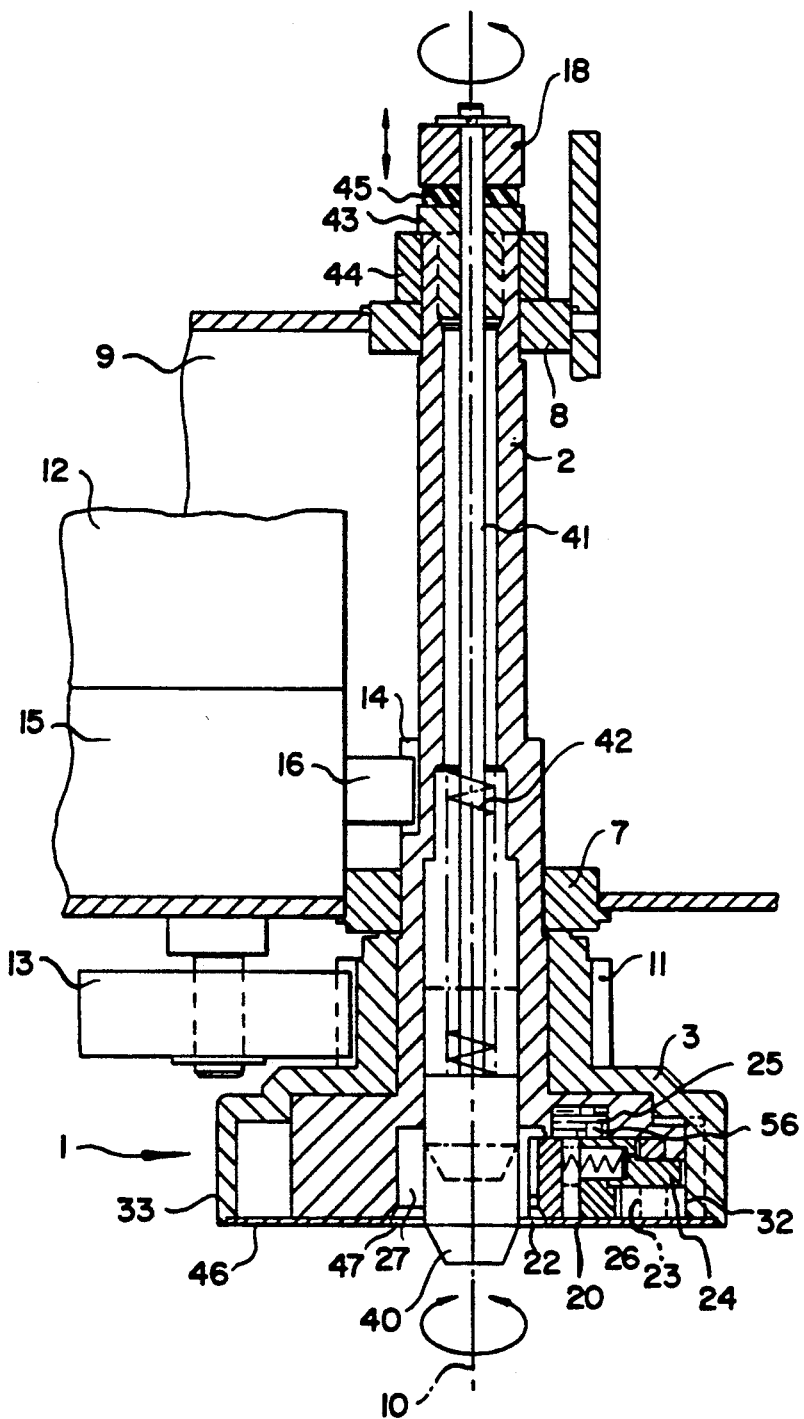
FIG. 4 is a lateral view according to FIG. 1 (cross-section along the line 4—4 in FIG. 2) of the gripper including a carrier member and a housing portion as well as an ejector.

FIG. 4 shows a cross-section of the gripper 1 according to FIGS. 1 and 2, wherein in particular arrangement and support of carrier member 2, housing portion 3 and ejector 17 are illustrated.

At its upper end portion above bearing 8, the carrier member 2 features a retaining ring 44 and a bearing sleeve 43 which holds the carrier member 2, is designed in the form of a hollow cylinder and consists of a shaft portion pressed into the axial bore of carrier member 2 and a flange portion supported by the retaining ring 44.

At the lower end portion of carrier member 2 a circular cover plate 46 is arranged whose bore 47 arranged coaxially with pivot 10 has a larger diameter than the maximum circular opening 27 formed by means of the clamping elements 20, 20', 20". Cover plate 46 covers the gripper 1 as far as the outer margin of housing portion 3, and, in addition, serves as a support plate for the clamping elements 20, 20', 20" and rollers 23, 23', 23".

Ejector 17 consists of a plunger 40 located in the area of the clamping elements 20, 20', 20" and a guide rod 41 on whose upper end portion stop member 18 is arranged.

Ejector 17 is supported, on the one hand, by bearing sleeve 43 via guide rod 41 and, on the other, in the area of the widened axial bore of carrier member 2 via plunger 40. Above plunger 40 a helical spring 42 is coaxially arranged on guide rod 41. Helical spring 42 rests on the upper end portion of the widened axial bore and urges the ejector 17 into its lower home position, the plunger 40 extending through bore 47 of cover plate 46 and projecting from gripper 1, and stop member 18 resting on bearing sleeve 43 via a damping washer 45.

At its lower end, plunger 40 has a diameter which is smaller than the smallest admissible diameter of a stopper 5.

The device operates as follows: First, a container 4 having a stopper 5 and held in tray 6 is pivoted into the processing position beneath gripper 1 by using a microprocessor-controlled transport means (not illustrated)—see FIG. 1.

Then container 4 is engaged by the grip arms 71 and 72 of the gripping device 70 and, by means of the lifting means 60, lifted from tray 6 to the extent that stopper 5 projects completely into the engaging range of the clamping elements 20, 20', 20" of gripper 1.

Ejector 17 is thereby moved to its upper end position and actuates switch 19 by means of its stop member 18. The signal produced by switch 19 stops the drive motor 64 and, thus, lifting means 60 and starts the microprocessor-controlled stepping motor 12.

Thereupon stepping motor 12 rotates housing portion 3 of gripper 1 counterclockwise until clamping elements 20, 20', 20", i.e. the rollers 23, 23', 23", have moved from cam section 33, 33', 33" to the outer radial contact position of section 32, 32', 32" shown in FIG. 2.

By means of locking pin 16 of the electromagnet carrier member 2 is secured against rotation as the locking pin extends into groove 14 (see FIGS. 1 and 4).

The inner end portions 22, 22', 22" of the clamping elements 20, 20', 20" now embrace and clamp the rubber or plastic stopper 5, the pointed protuberances 52 shown in FIG. 3 piercing into the stopper and, thus, forming a positive engagement therewith.

Subsequently, the microprocessor-controlled electromagnet 15 is energized and, as a result, locking pin 16 is withdrawn from groove 14 of carrier member 2.

Then stepping motor 12 is turned on again and housing portion 3 as well as carrier member 2 together with stopper 5 are continued to be rotated counterclockwise. Such entrainment of carrier member 2 is effected by its stop means 29, 29', 29" and the partitions 37, 37', 37" of housing portion 3 (see FIG. 2). As stopper 5 is rotated in the opening of container 4, container 4 is pulled downwards and replaced in tray 6. This is effected by lowering the lifting means 60 (see FIG. 1).

When container 4 has been disengaged by opening the grip arms 71 and 72, it is pivoted together with tray 6 to an aspirating station for sample fluids.

In case, part of the sample fluid is to be kept in container 4 for subsequent analyses, container 4 is pivoted back beneath gripper 1 and re-closed with stopper 5 which was held in the gripper. This is effected in that gripper 1 together with stopper 5 is again rotated counterclockwise and container 4 is engaged by grip arms 71, 72, raised by the lifting means 60 and its opening is pushed over the stopper from below. Then stepping motor 12 and electromagnet 15 are turned off.

For disengaging stopper 5, the stepping motor 12 is again switched on, but with its direction of rotation and thus, that of the gripper 1 reversed. As carrier member 2 is blocked by locking pin 16, only housing portion 3 is rotated to the extent that clamping elements 20, 20', 20" with their rollers 23, 23', 23" have returned to the outer radial contact position of cam sections 33, 33', 33" clamping elements have been urged radially outwards by the spring elements 25, 25', 25" and 26, 26', 26" (see FIG. 2) therefore, enlarging the circumference of circular aperture 27'. When container 4 has been lowered into grip arms 71, 72 are disengaged therefrom the replacing operation of stopper 5 is terminated.

If container 4 is not to be re-closed, stopper 5 is thrown into a waste bin after container 4 has been pivoted to the aspirating station for sample fluids. Stopper 5 is thrown off by the clamping elements 20, 20', 20" disengaging therefrom and the ejector 17 pushing it out.

What is claimed is:

1. A device usable in an analyzer for removing and inserting a stopper from and into the opening of a container for liquids arranged in a tray and comprising
means for gripping a stoppered container,
a stopper gripper means frictionally interacting with the stopper,
means for feeding the container to the gripper means, the stopper gripper means comprising plural radially arranged clamping elements, and
means for radially moving said clamping elements into and out of engagement with a stopper; said means for moving said clamping elements having an inner and outer radial contact position and wherein said means for moving said clamping elements and said clamping elements remain coplanar to one another, said means for moving said clamping elements further comprising a plurality of control elements, each said control element including a first cam section having a small radius and defining said inner radial contact position, and a second cam section having a larger radius and defining said outer radial contact position, the control elements being coaxially arranged in the form of a ring, the device further comprising a carrier member and a cylindrical housing portion, said clamping elements being arranged on said carrier member and the control elements being coaxially mounted in said cylindrical housing section, the carrier member and the housing portion being rotatably mounted relative to each other and positively connected by means of a locking pin.

2. A device according to claim 1, wherein the housing portion includes a toothed rim on its periphery.

3. A device according to claim 1, and further including a microprocessor-controlled electromagnet that actuates said locking pin.

4. A device according to claim 1, and further including a microprocessor-controlled stepping motor that drives said housing portion.

* * * * *